United States Patent [19]

Fushimi et al.

[11] Patent Number: 5,060,517

[45] Date of Patent: Oct. 29, 1991

[54] IMMERSION TYPE AUTOMATIC ULTRASONIC TESTING APARATUS FOR DETECTING FLAWS OF BALLS

[75] Inventors: Koji Fushimi, Gifu; Shigeo Nishioka; Kazuhiro Konishi, both of Nagoya, all of Japan

[73] Assignee: NGK Insulators, Ltd., Nagoya, Japan

[21] Appl. No.: 574,017

[22] Filed: Aug. 29, 1990

[30] Foreign Application Priority Data

Aug. 31, 1989 [JP] Japan ............................. 1-225016

[51] Int. Cl.⁵ .................. G01M 13/04; G01N 29/26; G01N 29/06
[52] U.S. Cl. .......................................... 73/620; 73/593; 73/598; 209/590; 209/905
[58] Field of Search ................ 73/593, 598, 600, 620, 73/627, 640, 571, 633; 209/590, 576, 905, 921, 599

[56] References Cited

U.S. PATENT DOCUMENTS

| | | | |
|---|---|---|---|
| 2,812,061 | 11/1957 | Pfister | 209/905 |
| 3,275,136 | 9/1966 | Allen et al. | 209/905 |
| 3,366,236 | 1/1968 | Breazeale | 209/905 |
| 4,281,548 | 8/1981 | Köber | 73/593 |
| 4,387,596 | 6/1983 | Fenkner et al. | 73/593 |
| 4,969,361 | 11/1990 | Kawasaki et al. | 73/593 |
| 5,001,674 | 3/1991 | Kawasaki | 73/640 |
| 5,005,417 | 4/1991 | Kawasaki et al. | 73/593 |

FOREIGN PATENT DOCUMENTS 63-243751 10/1988 Japan .

Primary Examiner—Hezron E. Williams
Assistant Examiner—Rose M. Finley
Attorney, Agent, or Firm—Armstrong, Nikaido, Marmelstein, Kubovcik & Murray

[57] ABSTRACT

An immersion type automatic ultrasonic testing apparatus for detecting flaws of balls comprising a tank for containing a liquid medium of transmitting ultrasonic wave, a ball rotating device for rotating a ball to be tested, an ultrasonic flaws detection device for detecting surface flaws in the ball while swiveling a probe around the ball rotated by the ball rotating device or rotating the ball spirally by the ball rotating device with or without swiveling the probe, and a ball feeding device for feeding the ball to the position of the ball rotating device. The ball feeding device comprises an air cylinder for holding the ball by suction at the tip thereof. For the suction holding of the ball at the tip of the air cylinder, a level regulating device is additionally provided for setting a level of the liquid medium of transmitting ultrasonic wave in the tank wherein the ball rotating device and the ultrasonic flaws detection device are placed.

7 Claims, 2 Drawing Sheets

IMMERSION TYPE AUTOMATIC ULTRASONIC TESTING APARATUS FOR DETECTING FLAWS OF BALLS

BACKGROUND OF THE INVENTION AND RELATED ART STATEMENT

This invention relates to an immersion type automatic ultrasonic testing apparatus for detecting flaws of balls, and more particularly to an immersion type automatic ultrasonic testing apparatus for balls which is capable of automatic and efficient detection flaws in the balls.

Tests on the surface and the inside part of balls used for structural members have hitherto been carried out by an X-ray testing, a fluorescent penetrate testing or by examining the appearance of the balls under a microscope or with the naked eye.

In the X-ray or fluorescent penetrate testing or the inspection of the appearance under a microscope or with the naked eye, however, the object of testing, i.e., the ball for structural member is rotated manually and, therefore, much time is required for testing the entire peripheral surface of the ball. In addition, there is a doubt whether the entire peripheral surface of the ball can always be tested completely.

In order to overcome the drawbacks of the conventional testing methods mentioned above, two of the inventors of this invention with other inventors have previously proposed, in U.S. Pat. No. 4,969,361, an ultrasonic testing method and apparatus by which the entire peripheral surface of a ball can be tested by placing the ball on drive rollers and rotating the ball.

SUMMARY OF THE INVENTION

It is an object of this invention to provide an ultrasonic testing apparatus for balls based on further improvements made in the ultrasonic testing method and apparatus disclosed in U.S. Pat. No. 4,969,361 so as to enable automatic testing with a further enhanced testing efficiency.

According to this invention, there is provided an immersion type automatic ultrasonic testing apparatus for detecting flaws of balls which comprises a tank for containing a liquid medium of transmitting ultrasonic wave, a ball rotating means for rotating a ball to be tested, an ultrasonic flaws detection means for detecting surface flaws in the ball, while in a liquid medium of transmitting ultrasonic wave swiveling a probe around the ball rotated by the ball rotating means or rotating the ball spirally rotated by the ball rotating means with or without swiveling the probe, and a ball feeding means for feeding the ball to the position of the ball rotating means, wherein the ball feeding means comprises an air cylinder for holding the ball by suction at the tip thereof.

In this invention, it is preferable, for the suction holding of the ball at the tip of the air cylinder, to provide additionally the liquid medium level regulating means for setting the liquid medium level below the ball rotating means when the ball held by suction at the tip of the air cylinder is placed onto the ball rotating means and when the ball is removed from the ball rotating means by the suction holding at the tip of the air cylinder, and for maintaining the liquid medium level above the ball and the probe during the defection of flaws in the ball by the ultrasonic flaws detection means.

As the liquid medium level regulating means, a mechanism can be preferably used which regulates the liquid medium level by raising or lowering a vessel of a predetermined volume in the tank. Where such a liquid medium level regulating mechanism is used, however, an attempt to regulate the liquid medium level in a shorter time for reducing the testing time would cause waving of the liquid medium surface or bubbling in the liquid medium, thereby causing adverse effects on the testing. That is to say, variations in the detection waveform or detection of the bubble as a flaw echo would occur. In the immersion type automatic ultrasonic testing apparatus for detecting flaws of balls according to this invention, therefore, it is preferable to provide a partition plate opened at a bottom portion thereof between the ultrasonic flaws detection means and the liquid medium level regulating mechanism, to form a bottom portion of the vertically movable vessel in a slant shape, or to take other similar measure, whereby the abovementioned bad effects can be obviated.

DETAILED DESCRIPTION OF THE PREFERRED EMBODIMENTS

Figure 1:
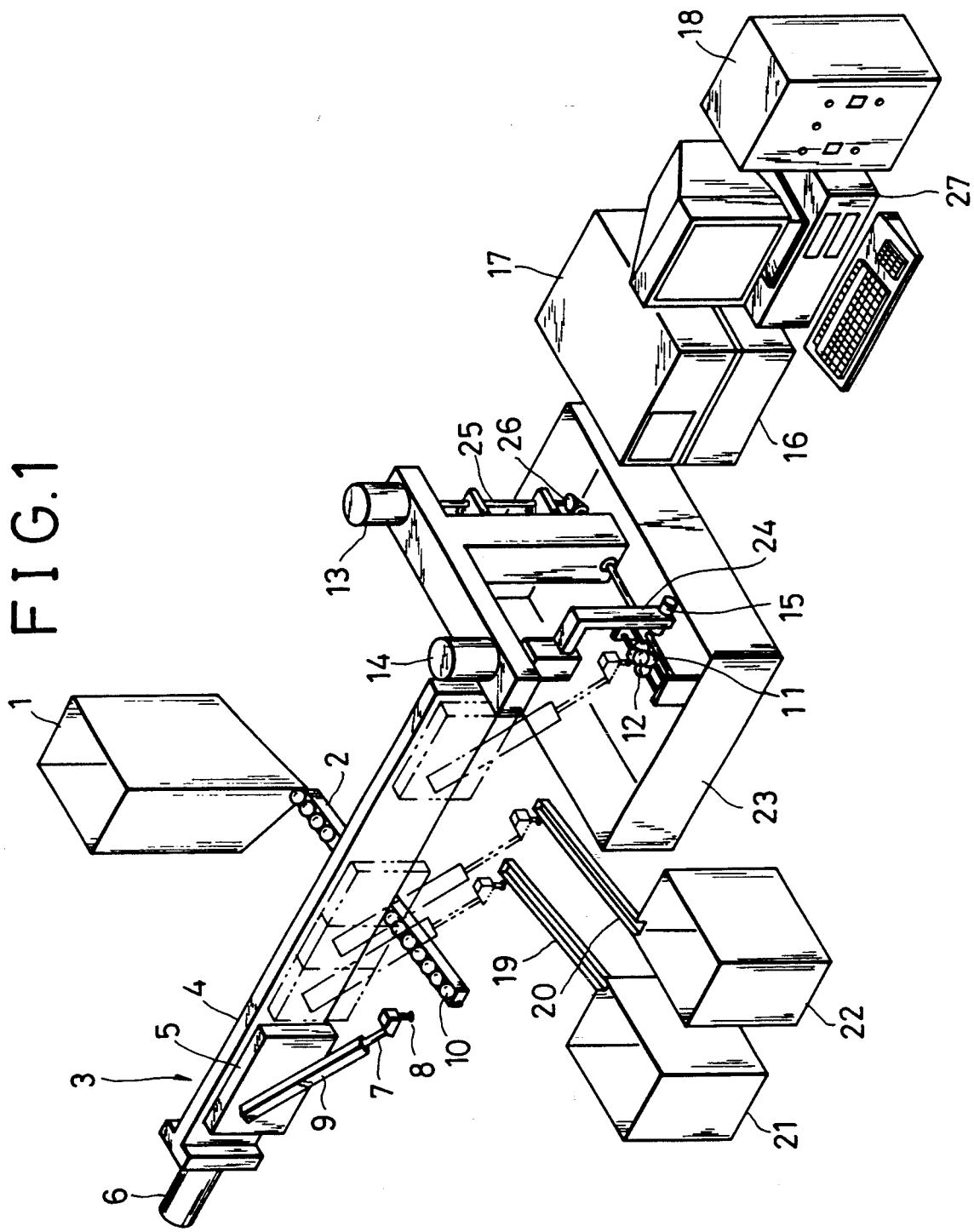
FIG. 1 is a perspective view of the total arrangement of one embodiment of an immersion type automatic ultrasonic testing apparatus for detecting flaws of balls according to this invention.

The ball as the material to be tested, namely, the object of the ultrasonic testing according to this invention is a ball used for a structural member, a wear-resistant member or a sliding member. This type of balls, whether made of ceramic or metal, can be used as the object of the ultrasonic testing of this invention, without any particular restrictions. However, ceramic balls are particularly effective for use as the object of the ultrasonic testing according to this invention, because the reliability of the ceramic balls is heavily dependent on the accurate detection of minute flaws in the surface and the sub-surface of the balls.

As the ceramic balls, those ceramic balls which comprise silicon nitride, silicon carbide, zirconia or alumina are preferably used, in view of the high strength and high hardness requirements of bearing members, wear-resistant members, sliding members, etc.

This invention will now be described more in detail while referring to the embodiments shown in the drawings; it is to be understood, however, that the invention is not limited to the embodiments.

FIG. 1 is a perspective view of the total arrangement of one embodiment of an immersion type automatic ultrasonic testing apparatus for detecting flaws of balls according to this invention.

In the FIG. 1, denoted by 1 is an untested ball supply container. The container 1 is charged with untested balls 10, which are aligned along an untested ball supply chute 2 slanted to the tip side thereof. Numeral 3 denotes a ball feeding device, which comprises a feed carriage 5 movable along a feed rail 4. The feed carriage 5 is capable of being moved along the rail 4 to, and stopped at, an arbitrary position by a feeding drive motor 6. To the feed carriage 5 is attached an air cylinder 9 which comprises a suction cup 8 capable of holding the ball by suction at the tip of a rod 7. The rod 7 is capable of being protruded from and retracted into the air cylinder 9, whereby the total length of the air cylinder 9 is variable.

At the start of ultrasonic testing of a ball, the feed carriage 5 is located at a position corresponding to the untested ball supply chute 2, whereas the rod 7 of the air cylinder 9 is located in a return end position (the upper end, in the figure) in which it is contained in the air cylinder 9, and a vacuum in the suction cup 8 is broken. Next, the rod 7 of the air cylinder 9 is extended to a forward end (the lower end, in the figure), and the suction cup 8 makes contact with the untested ball 10 located at the tip of the untested ball supply chute 2, when the suction cup 8 is operated to hold the ball 10 by suction. After the ball 10 is held by suction satisfactorily, the rod 7 of the air cylinder 9 is retracted, and the feed carriage 5 is moved to and stopped at a position corresponding to rollers 11 for rotating the ball under test. Then, the rod 7 of the air cylinder 9 is protruded to the forward end, and the untested ball 10 is placed on the rotating rollers 11 where the ball 12 setted under test, followed by cutting off the vacuum in the suction cup 8 and retraction of the rod 7 in the air air cylinder 9. The ultrasonic flaw detecting test is performed in a liquid medium of transmitting ultrasonic wave, for example, water, oil, etc. The following is a description of an example using water as the liquid medium. Before placing of the untested ball 10 on the rollers 11 for rotation of the ball under test, the water level in the tank 23 is preliminarily lowered below the rollers 11, by a water level regulating mechanism described later. After the untested ball 10 is placed on the rollers 11, on the other hand, the water level in the tank 23 is raised so that the water surface is located above a probe 15 and the ball 12 under test.

Then, a motor 13 for rotating the ball under test is operated to rotate the rollers 11 for rotating the ball under test, whereby the ball 12 under test is vertically or spirally rotated. Simultaneously, a probe swiveling motor 14 is rotated so that the probe 15 is horizontally swiveled 180° by a probe swiveling arm 24 when vertically or spirally rotating the ball 12, or the probe swiveling motor 14 is not operated so that the probe 15 is fixed without being swiveled when spirally rotating the ball 12. In the FIG. 1, numeral 25 denotes a shaft for transmitting a rotating force for the ball under test, and numeral 26 denotes a bevel gearing for transmitting the rotating force for the ball under test. The probe 15 is connected to an ultrasonic flaw detector 16, and detection of internal flaws in the ball 12 under test is carried out over the entire periphery of the ball. When a flaw is present in the ball, the flaw signal is observed on an oscilloscope 17 of the ultrasonic flaw detector 16, and a flaw signal is output to a mechanical drive, portion control panel 18. Besides, a computer 27 is provided for controlling the ultrasonic flaw detector 16 and analyzing the flaw detection data.

After the ultrasonic test on the entire periphery of the ball 12 under test is finished, the water level in the water tank 23 is lowered below the rotating rollers 11 for the ball under test by the water level regulating mechanism, which will be described later. Subsequently, the rod 7 of the air cylinder 9 is extended to the forward end to bring the suction cup 8 into contact with the ball 12 under test, and a vacuum is applied to hold the ball by suction. After the ball is held by suction satisfactorily, the rod 7 of the air cylinder 9 is retracted. When no flaw signal is obtained for the ball, the feed carriage 5 is moved to and stopped at the position of an accepted-ball discharge chute 19. When a flaw signal is obtained for the ball, on the other hand, the feed carriage 5 is moved to the position of a rejected-ball discharge chute 20, and stopped there. The rod 7 of the air cylinder 9 is protruded to the forward end over either of the discharge chutes, and the vacuum in the suction cup 8 is cut off to drop the ball. The ball is guided along the discharge chute, to be contained into an accepted-ball receiver 21 or a rejected-ball receiver 22.

After the ball is dropped, the rod 7 of the air cylinder 9 is retracted, and the feed carriage 5 is moved to and stopped at the initial position corresponding to the untested-ball supply chute 2.

Thereafter, the above process is repeated, whereby the ultrasonic test on the balls can be carried out automatically to separate accepted balls and rejected balls from each other.

Solenoid valves for operating the air cylinder and for the suction cup, limit switches for positioning mechanical drive portions, such as the feeding device, and the like, though not shown, are controlled appropriately by the mechanical drive portion control panel 18.

Now, the water level regulating mechanism for regulating the water level in the water tank 23 will be explained below.

Figure 2:
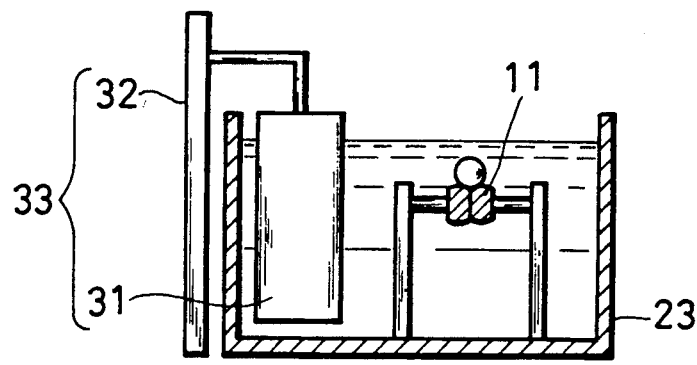
FIGS. 2 to 4 are each a schematic sectional view of one embodiment of a liquid medium of transmitting ultrasonic wave level regulating mechanism used in the immersion type automatic ultrasonic testing apparatus for detecting flaws of balls according to this invention.

FIG. 2 is a schematic sectional view of one embodiment of a water level regulating mechanism used in the immersion type automatic ultrasonic testing apparatus for detecting flaws of balls according to this invention. In this embodiment, a water level regulator 33 comprising a vessel 31 and a device 32 for moving the vessel 31 upward and downward is disposed at a side portion in the water tank 23.

In this case, the water level is lowered by moving the vessel 31 up above the water surface, and is raised by moving the vessel 31 down into the water.

Figure 3:
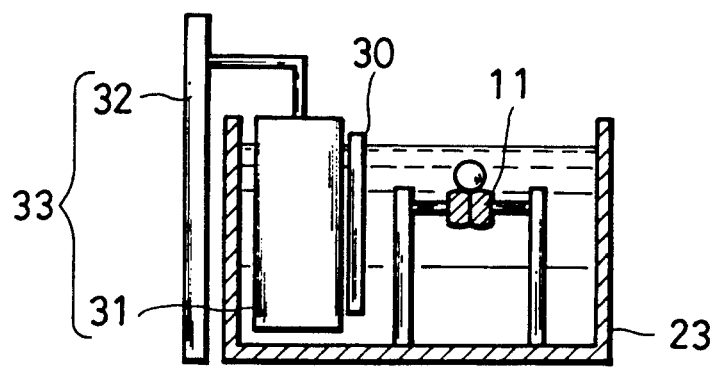

FIG. 3 is a schematic sectional view of another embodiment of the water level regulating mechanism used in the immersion type automatic ultrasonic testing apparatus for detecting flaws of balls according to this invention.

In this embodiment, the tank 23 is provided therein with a partition plate 30 opened at a bottom portion thereof, for separation between the zone of the water level regulator 33 and the zone of the ultrasonic flaw detection mechanism which comprises the rollers 11 for rotating the ball under test, the probe 15, the probe swiveling arm 24 (not shown in FIG. 3) and the like.

In this case, the partition plate 30 is opened at a bottom portion of the tank 23 to permit water to flow from one of the zones into the other and vice versa. With this construction, even when the vessel 31 is moved up or down speedily to regulate the water level, the partition plate 30 restrains the waving of the water surface or bubbling in the water in the zone of the ultrasonic flaw detection means. Therefore, the testing is not affected adversely by such waving or bubbling.

Figure 4:
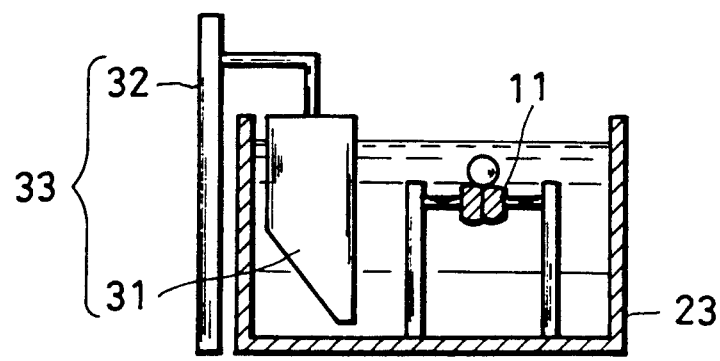

FIG. 4 is a schematic sectional view of a further embodiment of the water level regulating means, in which a bottom portion of the vessel 31 is formed in a slant shape.

In this embodiment, also, the waving of the water surface or generation of bubbles, at the time of regulation of the water level by moving the vessel 31 up or down, is restrained because the bottom portion of the vessel 31 is shaped aslant.

Forming the bottom portion of the vessel 31 in a slant shape may also be adopted in the embodiment illustrated in FIG. 3. In that case, a more favorable effects is obtained, from the viewpoint of restraint on the waving of the water surface or generation of bubbling.

As has been described above, the immersion type automatic ultrasonic testing apparatus for detecting flaws of balls according to this invention comprises fundamentally a ball rotating means, a ultrasonic flaw detection means and a ball feeding means, and is characterized in that an air cylinder for holding the ball by suction at the tip thereof is used as the ball feeding means.

After the ball is suction held by the tip of the air cylinder, the ball is fed to the position of the ball rotating device, and is placed on top of the ball rotating device. In this case, the water level is preliminarily lowered below the ball rotating device.

After the ball is thus placed on top of the ball rotating device, the water level is raised so that the water surface is located above the probe and the ball. Next, the test on the ball by the ultrasonic flaw detection device is carried out with the probe being swiveled around the ball, or with the probe being fixed and the ball being spirally rotated. The test is performed by transmitting an ultrasonic wave toward the ball through the liquid medium, receiving an ultrasonic echo reflected back from the ball, and observing the waveform of the echo signal on the ultrasonic flaw detector connected to the probe, thereby detecting surface flaws in the ball.

When the test on the ball is finished, the air cylinder of the ball feeding device holds by suction the tested ball on the ball rotating device, and removes the ball therefrom to a predetermined place. The air cylinder then holds by suction a new ball to be tested, and feeds the ball onto the ball rotating device, followed by the testing.

In this manner, a predetermined number of balls to be tested are capable of being tested, completely over the entire periphery thereof, automatically and speedily.

What is claimed is:

1. An immersion type automatic ultrasonic testing apparatus for detecting flaws in balls which comprises:
    a tank for containing a liquid medium for transmitting ultrasonic waves;
    a ball rotating means for rotating a ball to be tested;
    an ultrasonic flaws detection means, comprising an ultrasonic probe, for detecting flaws in the ball rotated by the ball rotating means;
    a ball feeding means for feeding the ball to the ball rotating means, the ball feeding means comprising an air cylinder for holding the ball by suction at the tip thereof, the ball rotating means and the probe being immersed in the liquid medium contained in the tank when detecting flaws;
    a liquid level regulating means for setting a level of the liquid medium in the tank below the ball when the ball held by suction at the tip of the air cylinder is placed onto the ball rotating means and when the ball is removed from the ball rotating means by suction at the tip of the air cylinder, and for maintaining the level above the ball and the probe during the detection of flaws in the ball by the ultrasonic flaws detection means.

2. An apparatus according to claim 1, wherein the liquid medium level regulating means controls the level by raising or lowering a vessel of a predetermined volume in the tank.

3. An apparatus according to claim 2, wherein a partition plate opened at a bottom portion thereof is disposed in the tank so as to separate the liquid medium level regulating means and the ultrasonic flaw detection means from each other.

4. An apparatus according to claim 2, wherein a bottom portion of the vessel is formed in a slant shape.

5. An apparatus according to claim 1, comprising means for swiveling said probe around the ball rotated by said ball rotating means.

6. An apparatus according to claim 1, wherein said ball rotating means rotates said ball spirally.

7. An apparatus according to claim 5, wherein said ball rotating means rotates said ball spirally while said probe is swiveled around said ball.

* * * * *

UNITED STATES PATENT AND TRADEMARK OFFICE
CERTIFICATE OF CORRECTION

PATENT NO. : 5,060,517

DATED : October 29, 1991

INVENTOR(S) : Koji FUSHIMI et al

It is certified that error appears in the above-identified patent and that said Letters Patent is hereby corrected as shown below:

On the cover page, Item [54], second line, "APARATUS" should read -- APPARATUS --.

Signed and Sealed this

Twenty-fifth Day of February, 1992

Attest:

HARRY F. MANBECK, JR.

*Attesting Officer*        *Commissioner of Patents and Trademarks*